(12) United States Patent
Misumi et al.

(10) Patent No.: US 11,089,805 B2
(45) Date of Patent: Aug. 17, 2021

(54) MUCOSAL IMMUNOMODULATOR

(71) Applicants: Yamada Bee Company, Inc., Okayama (JP); National University Corporation Kumamoto University, Kumamoto (JP)

(72) Inventors: Shogo Misumi, Kumamoto (JP); Tomoki Ikuta, Okayama (JP); Tomoki Tatefuji, Okayama (JP); Hiroko Tani, Okayama (JP); Hiroshi Inooka, Okayama (JP)

(73) Assignees: Yamada Bee Company, Inc., Okayama (JP); National University Corporation Kumamoto University, Kumamoto (JP)

( * ) Notice: Subject to any disclaimer, the term of this patent is extended or adjusted under 35 U.S.C. 154(b) by 195 days.

(21) Appl. No.: 16/343,393

(22) PCT Filed: Oct. 12, 2017

(86) PCT No.: PCT/JP2017/037056
§ 371 (c)(1),
(2) Date: Apr. 18, 2019

(87) PCT Pub. No.: WO2018/074327
PCT Pub. Date: Apr. 26, 2018

(65) Prior Publication Data
US 2019/0230967 A1 Aug. 1, 2019

(30) Foreign Application Priority Data
Oct. 20, 2016 (JP) ............................ JP2016-206134

(51) Int. Cl.
| | | |
|---|---|---|
| *A61K 31/22* | (2006.01) | |
| *A61K 31/201* | (2006.01) | |
| *A23L 33/12* | (2016.01) | |
| *A61P 37/06* | (2006.01) | |
| *A61K 31/191* | (2006.01) | |
| *A61K 31/231* | (2006.01) | |
| *A61P 37/04* | (2006.01) | |
| *A61K 31/194* | (2006.01) | |
| *A61K 39/39* | (2006.01) | |
| *A61P 37/02* | (2006.01) | |

(52) U.S. Cl.
CPC ............ *A23L 33/12* (2016.08); *A61K 31/191* (2013.01); *A61K 31/194* (2013.01); *A61K 31/231* (2013.01); *A61K 39/39* (2013.01); *A61P 37/02* (2018.01); *A61P 37/04* (2018.01); *A61P 37/06* (2018.01); *Y02A 50/30* (2018.01)

(58) Field of Classification Search
CPC .............................. A61K 31/22; A61K 31/201
USPC .................................................. 514/546, 560
See application file for complete search history.

(56) References Cited

U.S. PATENT DOCUMENTS 8,119,839 B2 * 2/2012 Yoshimura .............. C07C 59/42
562/598

FOREIGN PATENT DOCUMENTS

| CN | 102206151 A | 10/2011 |
|---|---|---|
| CN | 103787879 A | 5/2014 |
| EP | 1316314 A1 | 6/2003 |
| JP | 2010/168290 A | 8/2010 |
| JP | 2011/084525 A | 4/2011 |
| TW | I247607 B | 1/2006 |
| WO | WO 02/17961 A1 | 3/2002 |
| WO | WO 2015/109979 A1 | 7/2015 |
| WO | WO 2016/170959 A1 | 10/2016 |

OTHER PUBLICATIONS

International Search Report dated Jan. 9, 2018 for International Patent Application No. PCT/JP2017/037056, 2 pages.
International Preliminary Report on Patentability dated Jan. 9, 2018 for International Patent Application No. PCT/JP2017/037056, 16 pages.
Famularo, et al: "Immunopharmacological profile of sebacic acid, a candidate for total parenteral nutrition", 1993 EOS—Rivista di Journal of Immunologia ed Immunofarmacologia, vol. 13, No. 2, pp. 142-145, Abstract.

(Continued)

*Primary Examiner* — Raymond J Henley, III
(74) *Attorney, Agent, or Firm* — Squire Patton Boggs (US) LLP (57) ABSTRACT

The present invention provides a mucosal immunomodulator comprising, as an active ingredient, at least one selected from the group consisting of compounds represented by the following formula (1), compounds represented by the following formula (2) and compounds represented by the following formula (3), and salts thereof.

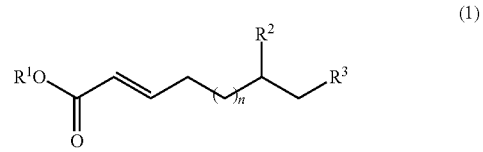

(1)

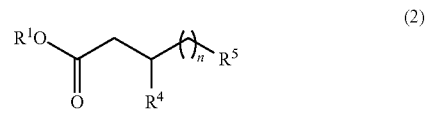

(2)

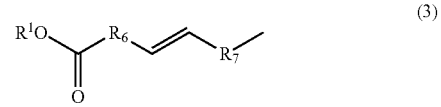

(3)

10 Claims, 4 Drawing Sheets

(56) References Cited

OTHER PUBLICATIONS

Gasic, et al: "Evaluation of the immunomodulatory activities of royal jelly components in Vitro", Immunopharmacology and Immunotoxicology 2007, vol. 29, No. 3-4, pp. 521-536, Abstract.
Kanaya, et al: "The mechanisms of M-cell differentiation", Bioscience of Microbiota, Food and Health, May 9, 2014, vol. 33, No. 3, pp. 91-97.
Mabbott, et al: "Microfold (M) cells: important immunosurveillance posts in the intestinal epithelium", Nature Review Jul. 2013, vol. 6, No. 4, pp. 666-677.
Nagai, et al: "Anti-allergic activity of a Kampo (Japanese herbal) medicine "Sho-seiryu-to (Xiao-Qing-Long-Tang)" on airway inflammation in a mouse model", International Immunopharmacology 2004, vol. 4, No. 10, pp. 1353-1365.
Nagai, et al: "Pinellic acid from the tuber of *Pinellia ternate* Breitenbach as an effective oral adjuvant for nasal influenza vaccine", International Immunopharmacology 2002, vol. 2, No. 8, pp. 1183-1193, Abstract, Fig. 1.
Saito, et al: "Search for novel mucosal membrane immune stimulators targeting cells", The 134th Meeting of the Pharmaceutical Society of Japan 2014, vol. 134, No. 30Y-PM10S, entire text.
Shimizu, et al: "Innovation of vaccine adjuvants", Nippon Rinsho (Japanese Journal of Clinical Medicine) 2008, vol. 66, No. 10, pp. 1915-1921, Fig. 1.
Wu, et al: "The immunoregulative effect of royal jelly acid", Journal of China Pharmaceutical University 1991, vol. 22, No. 2, pp. 117-118, Abstract.
Communication forwarding the extended European search report dated May 28, 2020 for European Patent Application No. 17861843.5, 13 pages.
Bergfeld, et al, "Re-Review Supplement Book 2: Alkyl Esters", Dec. 14, 2010; pp. 1-393, XP055694364.
Kai, et al, "Royal jelly enhances antigen-specific mucosal IgA response", Food Science & Nutrition, Mar. 6, 2013; vol. 1, No. 3, pp. 222-227, XP055689695.
Nagai, et al, "Oral adjuvant activity for nasal influenza vaccines caused by combination of two trihydroxy fatty acid stereoisomers from the tuber of *Pinellia ternata*", International Immunopharmacology, Jun. 1, 2010; vol. 10, No. 6, pp. 655-661, XP055694500.
Nagai, et al, "Intranasally and orally effective adjuvants from Chinese and Japanese medicinal herbs for nasal influenza vaccine", Acta Horticulturae, Feb. 1, 2005; No. 679, pp. 121-129, XP055694498.
Shirahata, et al, "Total synthesis, elucidation of absolute stereochemistry, and adjuvant activity of trihydroxy fatty acids", Tetrahedron, Oct. 2, 2006; vol. 62, No. 40, pp. 9483-9496, XP025002709.

\* cited by examiner

MUCOSAL IMMUNOMODULATOR

TECHNICAL FIELD

The present invention relates to a mucosal immunomodulator.

BACKGROUND ART

Mucous tissues such as the intestinal tract or respiratory organs, which is in contact with the external environment, become initial infection sites in many cases. Therefore, it is important, from the viewpoint of preventive medicine, to strengthen the mucosal immune function. As the front barrier of infection defense mechanism, Peyer patches and nasal-associated lymphoid tissue (NALT) play central roles in the induction and control of mucosal immune responses. Microfold cells (M cells) are found in gut-associated lymphoid tissue, such as Peyer patches, and the follicle-associated epithelium (FAE) covering lymphoid follicles, such as NALT. M cells are involved in the initiation of mucosal immune responses through the uptake and transcytosis of intestinal antigens (Non Patent Literature 1). Glycoprotein 2 (GP2) is known as an M cell-specific marker (Non Patent Literature 2).

As a mucosal immunostimulator, Patent Literature 1 discloses a mucosal immunostimulator comprising, as an active ingredient, at least one honeybee product selected from royal jelly, propolis, and bee pollen.

CITATION LIST

Patent Literature

Patent Literature 1: JP 2011-84525 A

Non Patent Literature

Non Patent Literature 1: Bioscience of Microbiota, Food and Health, 2014, Vol. 33 (No. 3), pp 91-97

Non Patent Literature 2: Mucosal Immunology, 2013, Vol. 6 (No. 4), pp. 666-677

SUMMARY OF INVENTION

Technical Problem

Some mucosal immunomodulators such as mucosal immunostimulators are known, as disclosed in Patent Literature 1; however, in order to satisfy various consumers' needs, it cannot be said that there have been sufficient options. Accordingly, an object of the present invention is to provide a novel mucosal immunomodulator.

Solution to Problem

The present invention relates to a mucosal immunomodulator comprising, as an active ingredient, at least one selected from the group consisting of compounds represented by the following formula (1):

[Chemical Formula 1]

(1)

wherein, in the formula (1), $R^1$ represents a hydrogen atom or an alkyl group having 1 to 3 carbon atoms, $R^2$ and $R^3$ each independently represent a hydrogen atom, a hydroxyl group or an alkylcarbonyloxy group having 2 to 4 carbon atoms, and n represents a natural number of 1 to 6;

compounds represented by the following formula (2):

[Chemical Formula 2]

(2)

wherein, in the formula (2), $R^1$ represents a hydrogen atom or an alkyl group having 1 to 3 carbon atoms, $R^4$ represents a hydrogen atom or a hydroxyl group, $R^5$ represents a hydroxyl group, a carboxyl group or an alkyloxycarbonyl group having 2 to 4 carbon atoms, and n represents a natural number of 1 to 9, provided that when $R^4$ is a hydrogen atom, $R^5$ is not a hydroxyl group;

compounds represented by the following formula (3):

[Chemical Formula 3]

(3)

wherein, in the formula (3), $R^1$ represents a hydrogen atom or an alkyl group having 1 to 3 carbon atoms, $R^6$ and $R^7$ each independently represent a linear alkylene group having 1 to 10 carbon atoms which may be substituted with hydroxyl group(s);
and salts thereof.

Because the mucosal immunomodulator of the present invention comprises, as an active ingredient, at least one selected from the group consisting of the compounds represented by the formula (1), formula (2) or formula (3), and salts thereof, it can modulate (stimulate or suppress) mucosal immunity.

It is preferable that the mucosal immunomodulator comprise, as an active ingredient, at least one selected from the group consisting of compounds represented by the following formulas (4), (5), (6), (7), (8), (9), (10), (11), (12), (13) or (14), and salts thereof. Mucosal immunity can thereby be further effectively modulated (stimulated or suppressed).

[Chemical Formula 4]

(4)

-continued

[Chemical Formula 5]

(5)

[Chemical Formula 6]

(6)

[Chemical Formula 7]

(7)

[Chemical Formula 8]

(8)

[Chemical Formula 9]

(9)

[Chemical Formula 10]

(10)

[Chemical Formula 11]

(11)

[Chemical Formula 12]

(12)

[Chemical Formula 13]

(13)

[Chemical Formula 14]

(14)

The mucosal immunomodulator of the present invention may be a mucosal immunostimulator comprising, as an active ingredient, at least one selected from the group consisting of the compounds represented by the above formula (4), formula (5), formula (6), formula (7) or formula (8), and salts thereof. Because these compounds stimulate mucosal immunity, they can be suitably used for mucosal immunostimulation.

The mucosal immunomodulator of the present invention may be a mucosal immunosuppressant comprising, as an active ingredient, at least one selected from the group consisting of the compounds represented by the above formula (9), formula (10), formula (11), formula (12), formula (13) or formula (14), and salts thereof. Because these compounds suppress mucosal immunity, they can be suitably used for mucosal immunosuppression.

The present invention also relates to a food composition for mucosal immunomodulation, comprising the above mucosal immunomodulator of the present invention. The food composition includes foods, health foods, foods with function claims, nutritional supplementary foods, supplements, and foods for specified health uses.

Because the food composition comprises the mucosal immunomodulator of the present invention, it has the function of modulating (stimulating or suppressing) mucosal immunity and can be suitably used for mucosal immunomodulation.

The present invention further relates to an adjuvant comprising the above mucosal immunostimulator. Because the above mucosal immunostimulator can induce the differentiation of M cells involved in the initiation of mucosal immune responses, it can be suitably used as an adjuvant.

The present invention further relates to a vaccine formulation comprising the above adjuvant.

The present invention can also be regarded as compounds represented by the formula (1), formula (2) or formula (3), or salts thereof for use in mucosal immunomodulation. The present invention can also be regarded as an agent comprising, as an active ingredient, at least one selected from the group consisting of the compounds represented by the formula (1), formula (2) or formula (3), and salts thereof for use in mucosal immunomodulation.

The present invention can also be regarded as application of the compounds represented by the formula (1), formula (2) or formula (3), or salts thereof in the production of a mucosal immunomodulator.

The present invention can also be regarded as a method for modulating mucosal immunity, the method comprising a step of administering an effective amount of a mucosal immunomodulator comprising, as an active ingredient, at least one selected from the group consisting of the compounds represented by the formula (1), formula (2) or formula (3), and salts thereof to a subject in need thereof.

Advantageous Effects of Invention

A novel mucosal immunomodulator is provided by the present invention. The mucosal immunomodulator of the present invention includes a mucosal immunostimulator stimulating mucosal immunity, and a mucosal immunosuppressant suppressing mucosal immunity. The mucosal immunostimulator of the present invention can induce the differentiation of M cells, and is thus useful as an adjuvant. The immunosuppressant of the present invention is useful for promoting immune tolerance.

DESCRIPTION OF EMBODIMENTS

Hereinafter, embodiments for carrying out the present invention are described in detail. However, the present invention is not limited to the following embodiments.

The mucosal immunomodulator of the present invention comprises, as an active ingredient, at least one selected from the group consisting of the compounds represented by the formula (1), the compounds represented by the formula (2) and the compounds represented by the formula (3), and salts thereof. Hereinafter, the compounds represented by the formula (1), the compounds represented by the formula (2) and the compounds represented by the formula (3) may also be collectively referred to as "the present compounds."

[Chemical Formula 15]

(1)

In the formula (1), $R^1$ represents a hydrogen atom or an alkyl group having 1 to 3 carbon atoms, $R^2$ and $R^3$ each independently represent a hydrogen atom, a hydroxyl group or an alkylcarbonyloxy group having 2 to 4 carbon atoms, and n represents a natural number of 1 to 6

Examples of the alkyl group having 1 to 3 carbon atoms in $R^1$ include a methyl group, an ethyl group, a 1-propyl group, and a 1-methylethyl group.

Examples of the alkylcarbonyloxy group having 2 to 4 carbon atoms in $R^2$ include a methylcarbonyloxy group ($CH_3-C(=O)-O-$), an ethylcarbonyloxy group ($CH_3-CH_2-C(=O)-O-$), 1-propylcarbonyloxy group ($CH_3-CH_2-CH_2-C(=O)-O-$), and a 1-methyl ethylcarbonyloxy group ($CH_3-CH(-CH_3)-C(=O)-O-$).

[Chemical Formula 16]

(2)

In the formula (2), $R^1$ has the same meaning as $R^1$ in the formula (1), $R^4$ represents a hydrogen atom or a hydroxyl group, $R^5$ represents a hydroxyl group, a carboxyl group or an alkyloxycarbonyl group having 2 to 4 carbon atoms, and n represents a natural number of 1 to 9, provided that when $R^4$ is a hydrogen atom, $R^5$ is not a hydroxyl group.

Examples of the alkyloxycarbonyl group having 2 to 4 carbon atoms in $R^5$ include a methyloxycarbonyl group ($CH_3-O-C(=O)-$), an ethyloxycarbonyl group ($CH_3CH_2-O-C(=O)-$), a 1-propyloxycarbonyl group ($CH_3-CH_2-CH_2-O-C(=O)-$) and a 1-methylethyloxycarbonyl group ($CH_3-CH(-CH_3-O-C(=O)-$).

It is preferable that n in the formula (2) be a natural number of 3 to 9 and it is more preferable that it be a natural number of 4 to 8.

[Chemical Formula 17]

(3)

In the formula (3), $R^1$ has the same meaning as $R^1$ in the formula (1) and $R^6$ and $R^7$ each independently represent a linear alkylene group having 1 to 10 carbon atoms which may be substituted with hydroxyl group(s).

Examples of the linear alkylene group having 1 to 10 carbon atoms in $R^6$ and $R^7$ include a methylene group, an ethylene group, an n-propylene group, an n-butylene group, an n-pentylene group, an n-hexylene group, an n-heptylene group, an n-octylene group, an n-nonylene group and an n-decylene group. The linear alkylene group having 1 to 10 carbon atoms in $R^6$ and $R^7$ may be substituted with hydroxyl group(s).

It is preferable that the linear alkylene group having 1 to 10 carbon atoms which may be substituted with hydroxyl group(s) in $R^6$ and $R^7$ be a linear alkylene group having 1 to 10 carbon atoms substituted with hydroxyl group(s), it is more preferable that it be a linear alkylene group having 3 to 9 carbon atoms substituted with hydroxyl group(s), it is even more preferable that it be a linear alkylene group having 5 to 8 carbon atoms substituted with hydroxyl group(s), it is even more preferable that it be a linear alkylene group having 6 to 8 carbon atoms substituted with hydroxyl group(s), and it is more preferable that it be a linear alkylene group having 6 to 8 carbon atoms substituted with 1 to 3 hydroxyl group(s).

When an optical isomer is present, the present compounds may be either of R-form or S-form. When a geometric isomer is present, the present compounds may be either of cis-form and trans-form.

More specific examples of the present compounds include the compounds represented by the following formula (4), (5), (6), (7), (8), (9), (10), (11), (12), (13) or (14).

[Chemical Formula 18]

(4)

[Chemical Formula 19]

(5)

[Chemical Formula 20]

(6)

-continued

[Chemical Formula 21]

(7)

[Chemical Formula 22]

(8)

[Chemical Formula 23]

(9)

[Chemical Formula 24]

(10)

[Chemical Formula 25]

(11)

[Chemical Formula 26]

(12)

[Chemical Formula 27]

(13)

[Chemical Formula 28]

(14)

The present compounds may be salts that are acceptable for food applications or pharmaceutical applications. Examples of salts of the present compounds include salts with alkali metals, alkaline earth metals, other metals, and ammonium. More specific examples of salts of the present compounds include potassium salts, sodium salts, calcium salts, and magnesium salts.

The present compounds and salts thereof can be produced, for example, according to the synthesis method of the compounds represented by the formula (4), (5), (6), (7), (8), (9), (10), (11), (12), (13) or (14) in the Examples described later. Moreover, the present compounds and salts thereof may be obtained, for example, by purification from natural products such as royal jelly. Furthermore, as the present compounds and salts thereof, commercially available products may be purchased and used.

The mucosal immunomodulator of the present invention may comprise one of the above present compounds and salts thereof singly or two or more in combination.

The compounds represented by the above formula (4), the formula (5), the formula (6), the formula (7) or the formula (8) stimulate mucosal immunity. Therefore, as one embodiment of the mucosal immunomodulator of the present invention, a mucosal immunostimulator comprising, as an active ingredient, at least one selected from the group consisting of the compounds represented by the formula (4), the formula (5), the formula (6), the formula (7) or the formula (8), and salts thereof, is provided.

The compounds represented by the above formula (9), the formula (10), the formula (11), the formula (12), the formula (13) or the formula (14) suppress mucosal immunity. Therefore, as one embodiment of the mucosal immunomodulator of the present invention, a mucosal immunosuppressant comprising, as an active ingredient, at least one selected from the group consisting of the compounds represented by the formula (9), the formula (10), the formula (11), the formula (12), the formula (13) or the formula (14), and salts thereof, is provided.

The mucosal immunomodulator of the present invention may comprise only the above active ingredient, or may further comprise other ingredients as long as the effects of the present invention are not impaired. Examples of other ingredients include pharmaceutically acceptable ingredients (e.g., diluents, binders, lubricants, disintegrators, emulsifiers, surfactants, bases, solubilizing agents, and suspending agents) and ingredients acceptable as food (e.g., minerals, vitamins, flavonoids, quinones, polyphenols, amino acids, nucleic acids, essential fatty acids, fresheners, binders, sweeteners, disintegrators, lubricants, coloring agents, flavoring agents, stabilizers, preservatives, sustained release controlling agents, surfactants, solubilizing agents, and wetting agents).

The mucosal immunomodulator of the present invention can be used, in terms of the amount of active ingredient, at a dose of 1 mg or more and 10 g or less per day for an adult with a body weight of 60 kg, preferably a dose of 5 mg or more and 8 g or less, more preferably a dose of 10 mg or more and 3 g or less, even more preferably a dose of 15 mg or more and 1.5 g or less, further more preferably a dose of 20 mg or more and 1 g or less, further even more preferably a dose of 22 mg or more and 500 mg or less, and particularly preferably a dose of 24 mg or more and 250 mg or less. The dose of the mucosal immunomodulator of the present invention when used in an infant may be, for example, ⅗ of the adult dose for infants at an age of 6 to less than 13 years old, ⅖ of the adult dose for infants at an age of 1 to less than 6 years old, and ⅕ of the adult dose for infants at an age of less than 1 year old. This dose can be suitably determined within the above-mentioned range, depending on the factors such as health conditions of a person to take, administration route, combination with other agents, and the like.

The mucosal immunomodulator of the present invention may be orally administered (taken), or parenterally administered (e.g., intranasally administered). The mucosal immunomodulator of the present invention may be administered once a day, or administered in several times a day, such as twice a day or three times a day, as long as the amount of active ingredient per day is within the above range. It is preferable that the mucosal immunomodulator oaf the present invention be continuously administered. Mucosal immunomodulator effects (e.g., mucosal immunostimulating effects) are more significantly exhibited by continuous administration.

The mucosal immunomodulator of the present invention may be in any form, such as a solid, liquid, paste, or the like. Examples of the form of the mucosal immunomodulator of the present invention include uncoated pills, sugar-coated pills, granules, powders, tablets, and capsules (hard capsules, soft capsules, and seamless capsules). The mucosal immunomodulator of the present invention can be prepared by, for example, mixing an active ingredient, which is the compound according to the present invention or a salt thereof, with other ingredients, if necessary, and forming the mixture into a dosage form mentioned above.

The mucosal immunomodulator of the present invention can be used as it is as a drug, a quasi-drug, or a food composition, and also can be used as an additive for drugs, quasi-drugs, and food compositions. It is preferable that the food composition be food in which the third function (physical condition-controlling function) of food is strengthened. Examples of the food in which the third function of food is strengthened include health foods, foods with function claims, nutritional supplementary foods, supplements, and foods for specified health uses.

A drug, a quasi-drug, or a food composition, each of which consists of the mucosal immunomodulator of the present invention, or a drug, a quasi-drug, or a food composition, each of which comprises the mucosal immunomodulator of the present invention, may be used for mucosal immunomodulation, may also be used for mucosal immunostimulation and may be labelled with the following indications: "increasing immune activity," "making the body resistant to viruses," "supporting immune function," "being useful to increase M cells," "keeping immune activity," "maintaining immune activity," "being suitable for people who easily catch cold," "making immune function excellent," "being useful to prevent weakened immune systems from being further weakened," "making the body resistant to food-poisoning bacteria," "supporting the health of the mucosa," "supporting mucosal immunity," "supporting the health of the nose and throat," "being useful for maintenance of health during winter," "being useful for maintenance of health in cold seasons," "making the body withstanding cold seasons," "modulating immune function," "inhibiting excess M cells," "suppressing excessive immune response," "preventing or improving bronchial asthma," "preventing or improving allergic rhinitis," "preventing or improving hay fever," "preventing or improving Crohn's disease," and the like.

The content of the mucosal immunomodulator of the present invention in drugs, quasi-drugs, and food compositions may be suitably determined depending on the type of drug, quasi-drug, and food composition, etc., so that the amount of active ingredient taken per day is within the above range.

When the mucosal immunomodulator of the present invention is used as it is as a food composition, or used as an additive for a food composition, the form of the food composition is not particularly limited, and examples thereof include beverages (soft drinks such as coffee, juice, and tea, milk drinks, lactic acid bacteria drinks, yogurt drinks, carbonated drinks, etc.) spreads (custard cream, etc.); pastes (fruit paste, etc.); Western confectionary (chocolates, doughnuts, pies, cream puffs, gums, jellies, candies, cookies, cakes, puddings, etc.); Japanese confectionary (daifuku, mochi, manju, castella, anmitsu, yokan, etc.); frozen desserts (ice cream, popsicle, sherbet, etc.); food products (curry, beef bowl, porridge, mise soup, soup, meat sauce, pasta, pickles, jams, etc.); and seasonings (dressing, furikake, tasty seasoning, soup stock, etc.).

When the mucosal immunomodulator of the present invention is used as it is as food in which the third function of food is strengthened (e.g., health foods, foods with function claims, nutritional supplementary foods, supplements, or foods for specified health uses), or used as an additive for food in which the third function of food is strengthened, examples of the form of the food in which the third function of food is strengthened include, in addition to the above forms of food, uncoated pills, sugar-coated pills, granules, powders, tablets, and capsules (hard capsules, soft capsules, and seamless capsules).

When the mucosal immunomodulator of the present invention is used as it is as a drug or a quasi-drug, or when the mucosal immunomodulator of the present invention is used as an additive for a drug or a quasi-drug, the form of the drug or quasi-drug is not particularly limited, and examples thereof include uncoated pills, sugar-coated pills, granules, powders, tablets, and capsules (hard capsules, soft capsules, and seamless capsules).

The method for producing drugs, quasi-drugs, or food compositions, to each of which the mucosal immunomodulator of the present invention is added, is not particularly limited, and can be suitably performed according to a known method. For example, drugs, quasi-drugs, or food compositions used for the above applications can be obtained by, for example, mixing the mucosal immunomodulator of the present invention with intermediate products or final products in the production process of the drugs, quasi-drugs, or food compositions.

The present invention can also be regarded as compounds represented by the above formula (1), formula (2) or formula (3), or salts thereof for use in mucosal immunomodulation. The present invention can also be regarded as an agent comprising, as an active ingredient, at least one selected from the group consisting of the compounds represented by the above formula (1), formula (2) or formula (3), and salts thereof for use in mucosal immunomodulation. The present invention can also be regarded as application of at least one selected from the group consisting of the compounds represented by the above formula (1), formula (2) or formula (3), and salts thereof in the production of a mucosal immunomodulator.

The present invention can also be regarded as a method for modulating (stimulating or suppressing) mucosal immunity the method comprising a step of administering an effective amount of a mucosal immunomodulator comprising, as an active ingredient, at least one selected from the group consisting of the compounds represented by the above formula (1), formula (2) or formula (3), and salts thereof to a subject in need thereof. Examples of the subject include rodents, ungulates, carnivores, marsupials, and primates. The subject is preferably a mammal, such as a cynomolgus monkey or a human, and more preferably a human.

Vaccine Formulation

Among the mucosal immunomodulators of the present invention, those having a mucosal immunostimulating action (mucosal immunostimulator) can also be used as an adjuvant. At least part, of the action mechanism by the adjuvant of the present invention is based on the induction of differentiation of cells, which is involved in the initiation of mucosal immune responses. The adjuvant according to the present embodiment may be one comprising the above mucosal immunostimulator or one consisting of the above mucosal immunostimulator.

The vaccine formulation of the present invention comprises the above adjuvant. The adjuvant of the present invention can be combined with various immunogens to form vaccine formulations. The vaccine formulation of the present invention may be a mixture of the adjuvant and an immunogen, or the adjuvant and an immunogen may be separated so that they are mixed at the time of administration or separately administered. The vaccine formulation of the present invention may be used for treatment or for prevention.

The immunogen to be used in combination with the adjuvant of the present invention is not particularly limited, as long as it is an antigen that induces an immune response against mammals, such as humans. Specific examples of immunogens include one or more pathogenic microorganisms selected from the group consisting of influenza virus, rotavirus, adenovirus, norovirus, measles virus, rubella virus, mumps virus, AIDS virus, hepatitis virus, poliovirus, rabies virus, *Bordetella pertussis*, *Corynebacterium diphtheriae*, *Helicobacter pylori*, enterohaemorrhagic *Escherichia coli* (EHEC), *Chlamydia* protozoa, *Mycoplasma* protozoa, Malaria parasite, coccidium protozoa, and schistosome; antigens derived from these pathogenic microorganisms, prion proteins, and the like. These immunogens may be inactivated or not inactivated.

The quantitative ratio of immunogen and adjuvant in the vaccine formulation of the present invention can be suitably determined depending on the type of immunogen used, the purpose of vaccine formulation, etc. For example, the quantitative ratio may be 1:0.0001 to 1:110000 (weight ratio), and is preferably 1:0.1 to 1:10 (weight ratio).

The form of the vaccine formulation of the present invention may be liquid or powder. The form of the vaccine formulation of the present invention is not particularly limited, and examples thereof include uncoated pills, sugar-coated pills, granules, powders, tablets, and capsules (hard capsules, soft capsules, and seamless capsules).

Known stabilizers, preservatives, etc., may be contained in the vaccine formulation of the present invention. The vaccine formulation of the present invention can be produced by a known method. The vaccine formulation of the present invention may be administered orally or intranasally.

The vaccine formulation of the present invention can be administered by a method comprising a step of administering the adjuvant to a subject, and a step of administering an immunogen to the subject. Administration of the adjuvant and administration of an immunogen may be performed simultaneously or separately. For example, administration of the adjuvant can be previously performed, and administration of an immunogen can be then performed. Furthermore, administration of an immunogen can be performed in a timely manner while the adjuvant is continuously administered. It is preferable that the vaccine formulation of the present invention be used such that, for example, an immunogen is administered after the adjuvant is continuously administered. Induction of immune responses can thereby be further facilitated. As a specific example of an embodiment in which the adjuvant is continuously administered, administration of an effective amount per day is continued for 3 days or more, preferably 7 days or more, more preferably 14 days or more, and even more preferably 21 days or more. Administration may be conducted in several times a day, such as twice a day or three times a day, within the effective amount range per day.

The effective amount of the adjuvant is, in terms of the amount of active ingredient, a dose of 1 mg or more and 10 g or less per day for an adult with a body weight of 60 kg, preferably a dose of 5 mg or more and 8 g or less, more preferably a dose of 10 mg or more and 3 g or less, even more preferably a dose of 15 mg or more and 1.5 g or less, further more preferably a dose of 20 mg or more and 1 g or less, further even more preferably a dose of 22 mg or more and 500 mg or less, and particularly preferably a dose of 24 mg or more and 250 mg or less. The effective amount for an infant may be, for example, $3/5$ of the adult dose for infants at an age of 6 to less than 13 years old, $2/5$ of the adult dose for infants at an age of 1 to less than 6 years old, and $1/5$ of the adult dose for infants at an age of less than 1 year old. This dose can be suitably determined within the above-mentioned range, depending on the factors such as health conditions of a person to take, administration route, combination with other agents, and the like.

EXAMPLES

Hereinafter, the present invention is described in more detail based on Examples. However, the present invention is not limited to the following Examples.

Test Example 1: M-Cell Differentiation Induction Test—In Vitro Test

Preparation of the Test Compounds

The compounds represented by the formula (4), (5), (6), (7), (8), (9), (10), (11), (12), (13) or (14) were prepared as the test compounds.

Synthesis of the Compound Represented by the Formula (4)

The compound represented by the formula (4) ((2E,9R)-9-hydroxy-2-decenoic acid) was synthesized according to the method described in Preparation Example 14 of JP 2010-168290 A.

Synthesis of the Compound Represented by the Formula (5)

The compound represented by the formula (5) ((2E,9R)-methyl-9,10-dihydroxy-2-decenoate) was synthesized according to the method described in Preparation Example 11 of JP 2010-168290 A.

Synthesis of the Compound Represented by the Formula (6)

The compound represented by the formula (6) ((2E,11R)-11,12-dihydroxy-2-dodecenoic acid) was synthesized according to the method described in Preparation Example 6 of JP 2010-168290 A.

Isolation of the Compound Represented by the Formula (7)

The compound represented by the formula (7) ((2E)-3,10-dihydroxy-decanoic acid) was isolated from royal jelly according to the following method.

1500 mL of methanol was added to 200 g of dried royal jelly powder (from Pinghu in Zhejiang Province) and extracted for 12 hour while stirring at room temperature. The eluate was filtered under reduced pressure, and the solvent of the filtrate was distilled off under reduced pressure. The obtained residue (108.9 g) was purified by ODS column chromatography (column: Cosmosil 75C18-PREP column size: φ80×205 mm, eluent: 10%, 50% aqueous methanol solution, 2500 ml each (1250 mL×2 fractions), and was divided into a fraction 1 (first half of 10% methanol elution), 2 (second half of 10% methanol elution), 3 (first half of 50% methanol elution), and 4 (second half of 50% methanol elution). The fraction 4 was purified by silica gel column chromatography (column: Daiso gel IR-60, column size: φ26×150 mm, eluent: chloroform containing 5%, 10% methanol, 500 mL (50 mL×10 fractions), and the fourth eluted fraction of 10% was concentrated. This was purified again by silica gel column chromatography (column: Daiso gel IR-60, column size: φ26×100 mm, eluent: chloroform containing 10, 15% methanol, 300 mL (20 mL×15 fractions), and the 13th to 19th eluted fractions were collected to obtain 23.7 mg of the compound represented by the formula (7).

Acquisition of the Compound Represented by the Formula (8)

The compound represented by the formula (8) (sebacic acid) was purchased from Sigma-aldrich.

Synthesis of the Compound Represented by the Formula (9)

The compound represented by the formula (9) ((2E,7R)-7,8-dihydroxy-2-octenoic acid) was synthesized according to the method described in Preparation Example 5 of JP 2010-168290 A.

Synthesis of the Compound Represented by the Formula (10)

The compound represented by the formula (10) ((2Z,9R)-9,10-dihydroxy-2-decenoic acid) was synthesized according to the method described in Preparation Example 8 of JP 2010-168290 A.

Synthesis of the Compound Represented by the Formula (11)

The compound represented by the formula (11) ((2E)-7-acetoxy-2-heptenoic acid) was synthesized according to the method described in Preparation Example 15 of JP 2010-168290 A.

Synthesis of the Compound Represented by the Formula (12)

The compound represented by the formula (12) ((2E,9R)-9,10-diacetoxy-2-decenoic acid) was synthesized according to the method described in Preparation Example 12 of JP 2010-168290 A.

Synthesis of the Compound Represented by the Formula (13)

The compound represented by the formula (13) ((2E,9S)-9,10-dihydroxy-2-decenoic acid) was synthesized according to the method described in Preparation Example 2 of JP 2010-168290 A.

Acquisition of the Compound Represented by the Formula (14)

The compound represented by the formula (14) (9(S),12(S),13(S)-trihydroxy-10(E)-octadecenoic acid) was purchased from Larodan.

Cell Culture

As an in vitro M-cell model, Caco-2 cells derived from human intestinal epithelium cells were used. The Caco-2 cells were cultured in an MEM medium (produced by Nissui Pharmaceutical Co., Ltd.) supplemented with 20% fetal calf serum (FCS, produced by CANSERA INTERNATIONAL), 2 mM glutamine, (produced by Wako Pure Chemical Industries, Ltd.), and 0.1 mM nonessential amino acid (produced by Gibco) at 37° C. in the presence of 5% $CO_2$. The cells were subcultured within a range of logarithmic growth ($2.0 \times 10^5$ to $1.0 \times 10^6$ cells/mL). The cell concentration was determined by counting the number of living cells and the number of dead cells by the trypan blue staining method.

Fluorescence-Activated Cell Sorting (FACS) Analysis

The induction of the differentiation of M cells by each test compound was analyzed by FACS using GP2 as an indicator. Each test compound was prepared as a DMSO solution (10 mM). After the Caco-2 cells were seeded in a 6-well plate and allowed to form a single-layer film, each of the above test compounds was added so that the final concentration was 100 μM. The same amount of DMSO was added as a control. The medium was as described above. After addition, the cells were cultured at 37° C. in the presence of 5% $CO_2$ for 3 days. After culture, the cells were collected with 1 mM EDTA.2Na/PBS(−) (pH 7.2), and stained with rabbit anti-GP2 antibody (produced by IMGENEX) and Alexa 488-labeled anti-rabbit antibody (produced by Molecular probes). The stained cells were analyzed by FACS (produced by BECKMAN COULTER), and GP2 expression levels were quantified.

The quantitative values of GP2 expression level were calculated by the analysis software Flowjo from the histograms of FACS, and the relative values when the quantitative value of the control (DMSO only) is set to 1 were calculated. The results are shown in the following Table 1.

TABLE 1

| Test Compound | GP2 Expression Level (relative value when DMSO = 1) |
| --- | --- |
| Formula (4) | 1.72 |
| Formula (5) | 2.46 |
| Formula (6) | 4.03 |
| Formula (7) | 1.48 |
| Formula (8) | 1.45 |
| Formula (9) | 0.75 |
| Formula (10) | 0.83 |
| Formula (11) | 0.16 |
| Formula (12) | 0.48 |
| Formula (13) | 0.39 |
| Formula (14) | 0.74 |
| DMSO | 1.00 |

The compounds represented by the formula (4), (5), (6), (7) or (8) induced the expression of GP2. In particular, the compounds represented by the formula (5) or (6) intensely induced the expression of GP2. On the other hand, the compounds represented by the formula (9), (10), (11), (12), (13) or (14) suppressed the expression of GP2. In particular, the compounds represented by the formula (11), (12) or (13) intensely suppressed the expression of GP2. Based on the results of the References Examples, it is considered that GP2 is an M-cell specific marker, and that the expression induction of GP2 reflects the differentiation induction of M cells.

Reference Example: Verification of Mucosal Immunostimulation Effect by Induction of GP2 Expression in 10-Hydroxydecanoic Acid Reference Example 1: M-Cell Differentiation Induction Test in 10-Hydroxydecanoic Acid—In Vitro Test Cell Culture The same method as in Test Example 1 was performed.

Fluorescence Activated Cell Sorting (FACS) Analysis in 10-Hydroxydecanoic Acid

FACS analysis was performed in the same manner as in Test Example 1, except that 10-hydroxydecanoic acid (manufactured by SIGMA-ALDRICH) was used as the test compound. The quantitative values of GP2 expression level were calculated by the analysis software Flowjo from the histograms of FACS, and the relative values when the quantitative value of the control (DMSO only) is set to 1 were calculated. The results are shown in the following Table 2. 10-Hydroxydecanoic acid induced the expression of GP2.

TABLE 2

| Test Compound | GP2 Expression Level (relative value when DMSO = 1) |
|---|---|
| 10-Hydroxydecanoic Acid | 2.63 |
| DMSO | 1.00 |

Morphological Analysis

After the Caco-2 cells were seeded at $2\times10^5$ cells in a Transwell insert (6.5 mm Transwell, produced by Corning) and allowed to firm a single-layer film, 10-hydroxydecanoic acid (final concentration: 100 μm) was applied from the apical side of the single-layer film, and the cells were cultured at 37° C. in the presence of 5% $CO_2$ for 3 days. After culture, the single-layer film together with the membrane of the Transwell insert was cut, and the cell morphology was observed with an electron microscope (produced by JEOL).

Figure 1:
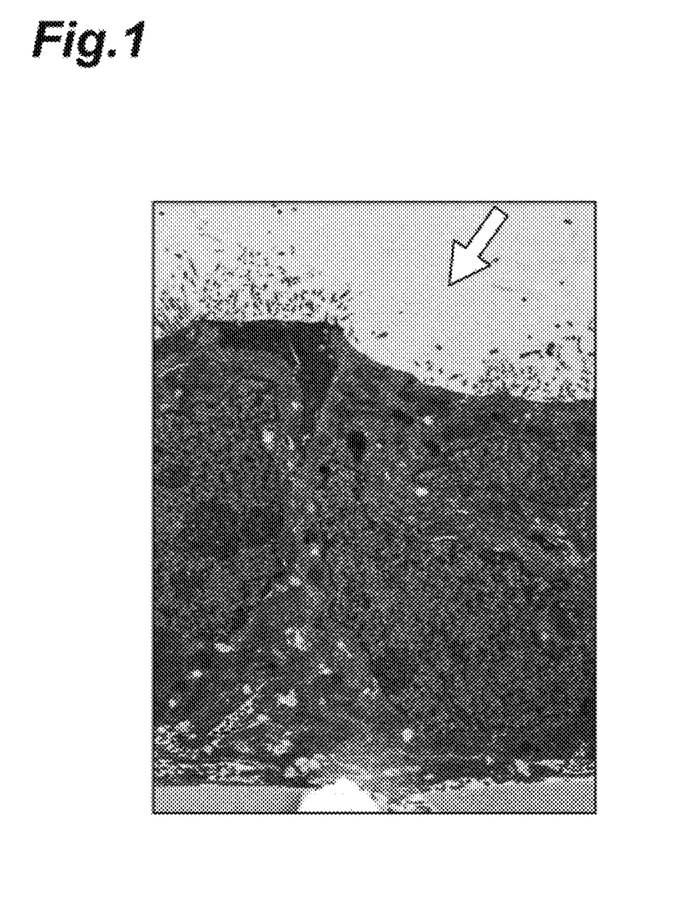
FIG. 1 is an electron micrograph showing the results of an M-cell differentiation induction test.

An electron micrograph is shown in FIG. 1. M cells generally have the morphological characteristics that microvilli on the apical side are shorter than those of epithelial cells in the vicinity thereof. As indicated by an arrow in FIG. 1, cells with short microvilli were observed due to the application of 10-hydroxydecanoic acid. From the results, it is considered to suggest that the Caco-2 cells were morphologically changed to M cell-like cells by the action of 10-hydroxydecanoic acid.

Reference Example 2: M-Cell Differentiation Induction Test in 10-Hydroxydecanoic Acid—In Vivo Test Test Method A DMSO solution (10 mM) of 10-hydroxydecanoic acid was diluted 100 times with PBS(-) to prepare a test solution. Three male cynomolgus monkeys (Macaca fascicularis) (age at the start of test: 3 to 4 years old, body weight at the start of test: 3.53 to 4.36 kg) were used as test animals. About 0.1 mL of the above test solution was sprayed to each of the left and right nasal cavities of each cynomolgus monkey using a fine atomizer (Neizaru) (product number: FAN020, produced and sold by Yoshikawa Kasei Co., Ltd.). The same operation was performed using PBS(-) as a control. After this operation was repeated once a day for 3 days, the cynomolgus monkeys were dissected on day 4, and the nasopharyngeal mucosa in the pharyngeal tonsil site was collected. The collected nasopharyngeal mucosa was subjected to fluorescent immunohistostaining with Alexa 555-labeled anti-GP2 antibody (produced by IMGENEX) or Alexa 555-labeled anti-GP2 antibody (produced by Abcam), and fluorescence images were observed with an all-in-one fluorescence microscope BZ-9000 (produced by Keyence Corporation). DAPI staining was used in combination for the observation of the fluorescence images.

Figure 2:
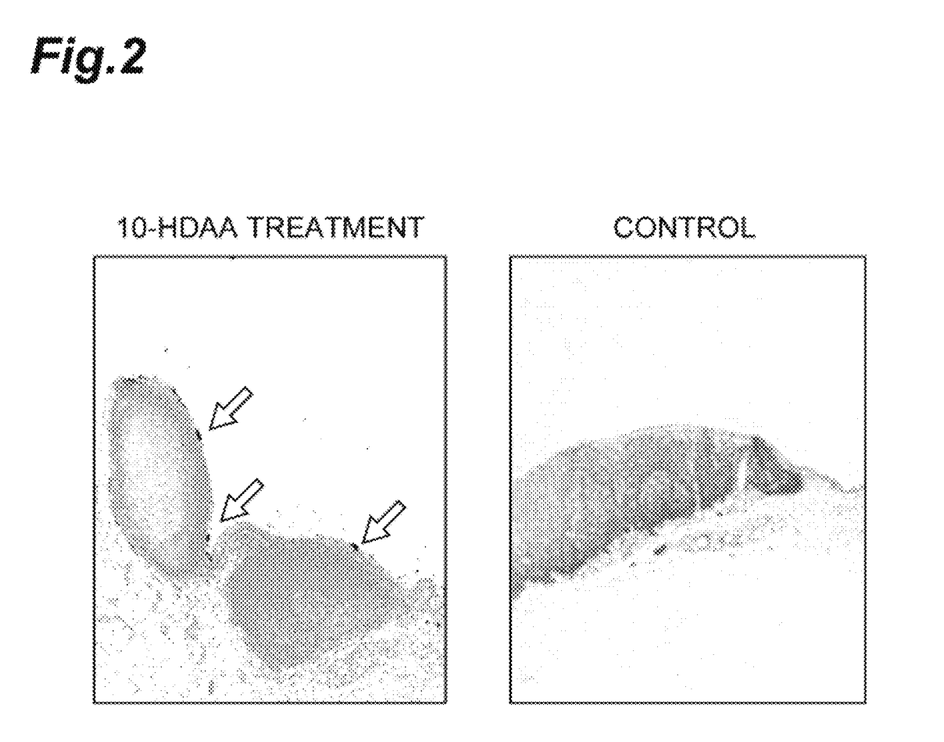
FIG. 2 is fluorescent immunohistostaining photographs showing the results of an M-cell differentiation induction test.

Fluorescent immunohistostaining photographs are shown in FIG. 2. In order to enhance the visibility of FIG. 2, light and darkness are reversed. As shown in FIG. 2, because the inside of the nasal cavities was exposed to 10-hydroxydecanoic acid for 3 days, GP2-positive cells (black portions shown by arrows in FIG. 2) were observed on the nasopharyngeal mucosa. In contrast, such an increase in GP2-positive cells was not observed in the control.

Reference Example 3: Immunostimulation Test in 10-Hydroxydecanoic Acid—In Vivo Test Test Method (Preparation of Capsules)

Only 2.4 mg of 10-hydroxydecanoic acid was placed in an enteric capsule to prepare a capsule containing 10-hydroxydecanoic acid (capsule A). In addition to 2.4 mg of 10-hydroxydecanoic acid, Fetuin (3 mg), an inactivated poliovirus antigen ($10^6$ $TCID_{50}$), and an inactivated influenza virus antigen (220_HA Units) were placed as antigens in an enteric capsule to prepare a capsule containing 10-hydroxydecanoic acid and the above 3 antigens (capsule B), Further, Fetuin (3 mg), an inactivated poliovirus antigen ($10^6$ $TCID_{50}$), and an inactivated influenza virus antigen (220_HA Units) were placed as antigens in an enteric capsule to prepare a capsule containing the above 3 antigens (capsule C).

Administration of Capsule

Three male cynomolgus monkeys (Macaca fascicularis) (age at the start of test: 3 to 6 years old, body weight at the start of test: 3.0 to 6.0 kg) were used as test animals, and the above capsule A and capsule B were orally administered according to the schedule shown in the following Table 3 (1 capsule once a day) (hereinafter, "the test group"). As a control, only the capsule C was orally administered to three male cynomolgus monkeys (age at the start of test: 3 to 6 years old, body weight at the start of test: 3.0 to 6.0 kg) according to the schedule shown in the following Table 3 (the capsule A and capsule B were not administered) (hereinafter, "the control group"). The cynomolgus monkeys were dissected on day 22, and the intestinal mucosa was collected. The collected intestinal mucosa was subjected to fluorescent immunohistostaining with Alexa 555-labeled anti-GP2 antibody (produced by IMGENEX) or Alexa 555-labeled anti-GP2 antibody (produced by Abeam), and fluorescence images were observed with an all-in-one fluorescence microscope BZ-9000 (produced by Keyence Corporation). DAPI staining was used in combination for the observation of the fluorescence images.

ELISA was stored in a chilling freezer. At the time of measurement, the sample for ELISA was diluted 10 times and 100 times with PBS(−).

TABLE 3

| | | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|---|
| Test Group | Capsule A (10-Hydroxydecanoic Acid) | ○ | — | ○ | ○ | — | ○ | ○ | ○ | — | ○ | ○ |
| | Capsule B (10-Hydroxydecanoic Acid + Ag) | — | ○ | — | — | ○ | — | — | — | ○ | — | — |
| Control Group | Capsule C (Ag) | — | ○ | — | — | ○ | — | — | — | ○ | — | — |

| | | Day 12 | Day 13 | Day 14 | Day 15 | Day 16 | Day 17 | Day 18 | Day 19 | Day 20 | Day 21 |
|---|---|---|---|---|---|---|---|---|---|---|---|
| Test Group | Capsule A (10-Hydroxydecanoic Acid) | — | ○ | ○ | ○ | — | ○ | ○ | — | ○ | ○ |
| | Capsule B (10-Hydroxydecanoic Acid + Ag) | ○ | — | — | — | ○ | — | — | ○ | — | — |
| Control Group | Capsule C (Ag) | ○ | — | — | — | ○ | — | — | ○ | — | — |

Ag: antigen,
○: administered,
—: not administered

Figure 3:
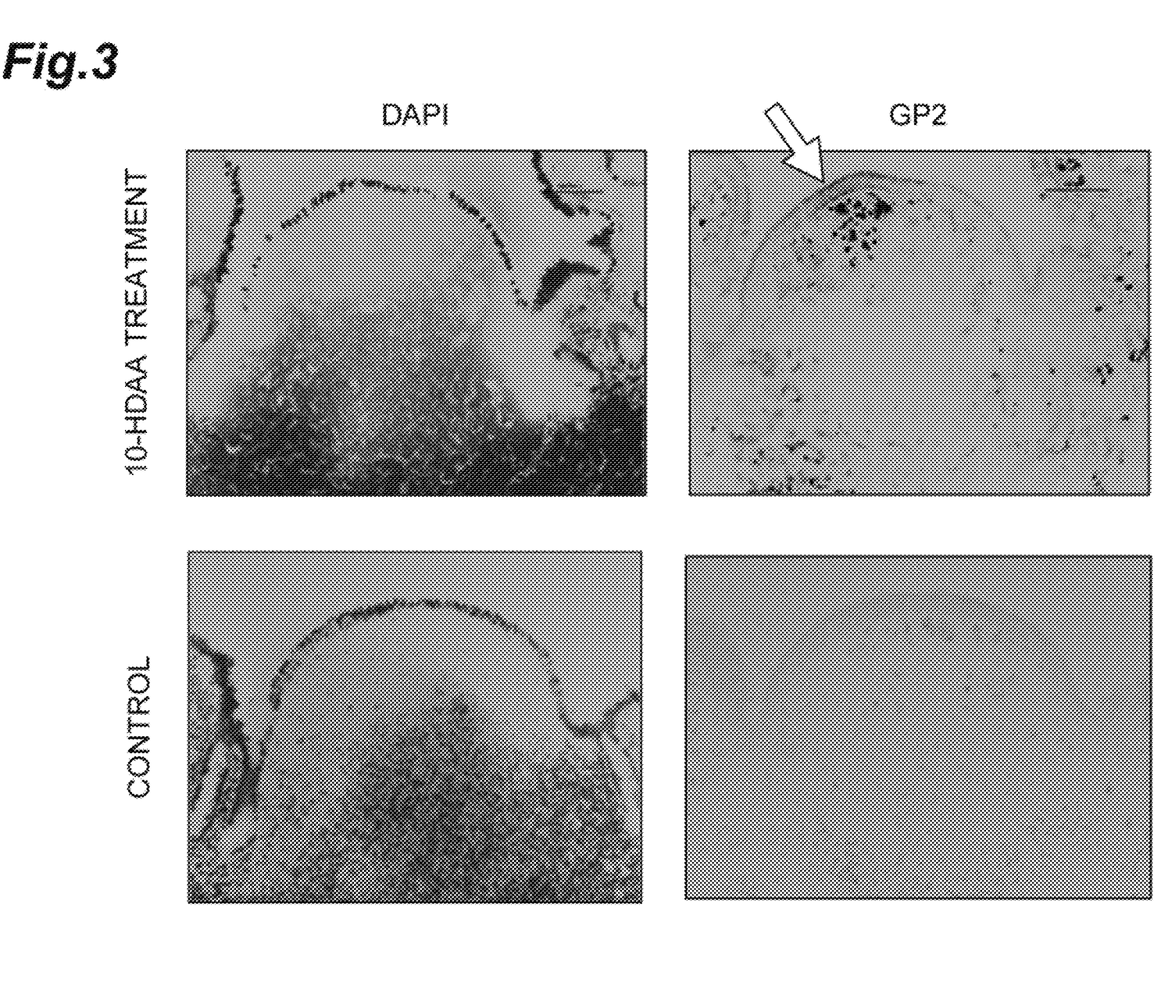
FIG. 3 is fluorescent immunohistostaining photographs showing the results of an immunostimulation test.

Examples of fluorescent immunohistostaining photographs are shown in FIG. 3. In order to enhance the visibility of FIG. 3, light and darkness are reversed. As shown in 3, GP2-positive cells (black portions shown by an arrow in FIG. 3) were observed on the intestinal mucosa in the test group, which was sensitized with the antigens about every 3 days while 10-hydroxydecanoic acid was continuously administered once a day. In contrast, such an increase in GP2-positive cells was not observed in the control group, which was sensitized only with the antigens about every 3 days.

Reference Example 4: Measurement of Antibody Titers in 10-Hydroxydecanoic Acid

Test Method

Feces of the cynomolgus monkeys raised in Reference Example 3 were collected, and the anti-Fetuin IgA antibody titer, anti-poliovirus IgA antibody titer, and anti-influenza virus IgA antibody titer in the feces were measured by ELISA.

Fetuin antigen (produced by Sigma) was dissolved at 100 μg/mL in an antigen buffer (50 mmol/L Tris-HCl (pH 8.0), 10 mmol/L $MgCl_2$, and 0.1% Tween 80). This antigen was added to a Nunc MaxiSorp (registered trademark) flat-bottom 96-well plate to prepare an antigen plate. Influenza virus H1N1 antigen (11,000 HA Unit) and poliovirus antigen type III (0.67×10⁸ $TCID_{50}$) were diluted with 25 mL of antigen buffer, and an antigen plate was prepared in the same manner as above. For masking, a reaction was performed at 200 μl/well at 4° C. overnight.

A sample buffer (0.1% sodium azide, 1 mmol/L EDTA.2Na, 0.05% Tween 20, 5% nonfat skim milk, and a PBS(−) (pH 7.2) solution of 1 mmol/L phenylmethylsulfonyl fluoride (PMSF)) was added to feces samples so that the weight ratio was 1:4. Antler the resultant was centrifuged at 13000×g for 5 minutes at 4° C., the supernatant was collected to prepare a sample for ELISA. The sample for The prepared sample was added in an amount of 50 μl to each well of the antigen plate, and shaken for 1.5 hours in a low-temperature room. Thereafter, washing was performed 4 times using a washing buffer (0.1% Tween 80 in 200 μl/well).

As a second antibody, BSA was dissolved in a second antibody buffer (0.5/M Tris-HCl 1.75% NaCl) to 1%, and the following antibodies (a) and (b) were diluted 5000 times with this buffer.

(a) Peroxidase-Labeled Affinity Purified antibody to Monkey IgA (alpha) (Cat. No. 074-11-011, KPL)

(b) Goat Anti-monkey IgA (alpha-chain specific)-peroxidase (Affinity purified) (Cat. No. 70041, Alpha diagnostic international)

The second antibody solution was added in an amount of 50 μl to each well, and reacted for 0.75 hours. After the reaction, washing was performed 4 times using a washing buffer (0.1% Tween 80 in MilliQ: 200 μl/well).

A substrate solution (2.68 mg of TMBZ, 1.05 μl of 35% hydrogen peroxide solution, and 7 mL of EDTA.2Na (2 mM)) was added in an amount of 50 μl to each well. Finally, 50 μl of 0.3N $H_2SO_4$ was added to each well to terminate the reaction. Thereafter, the absorbance (450 nm/630 nm) was measured.

Figure 4:
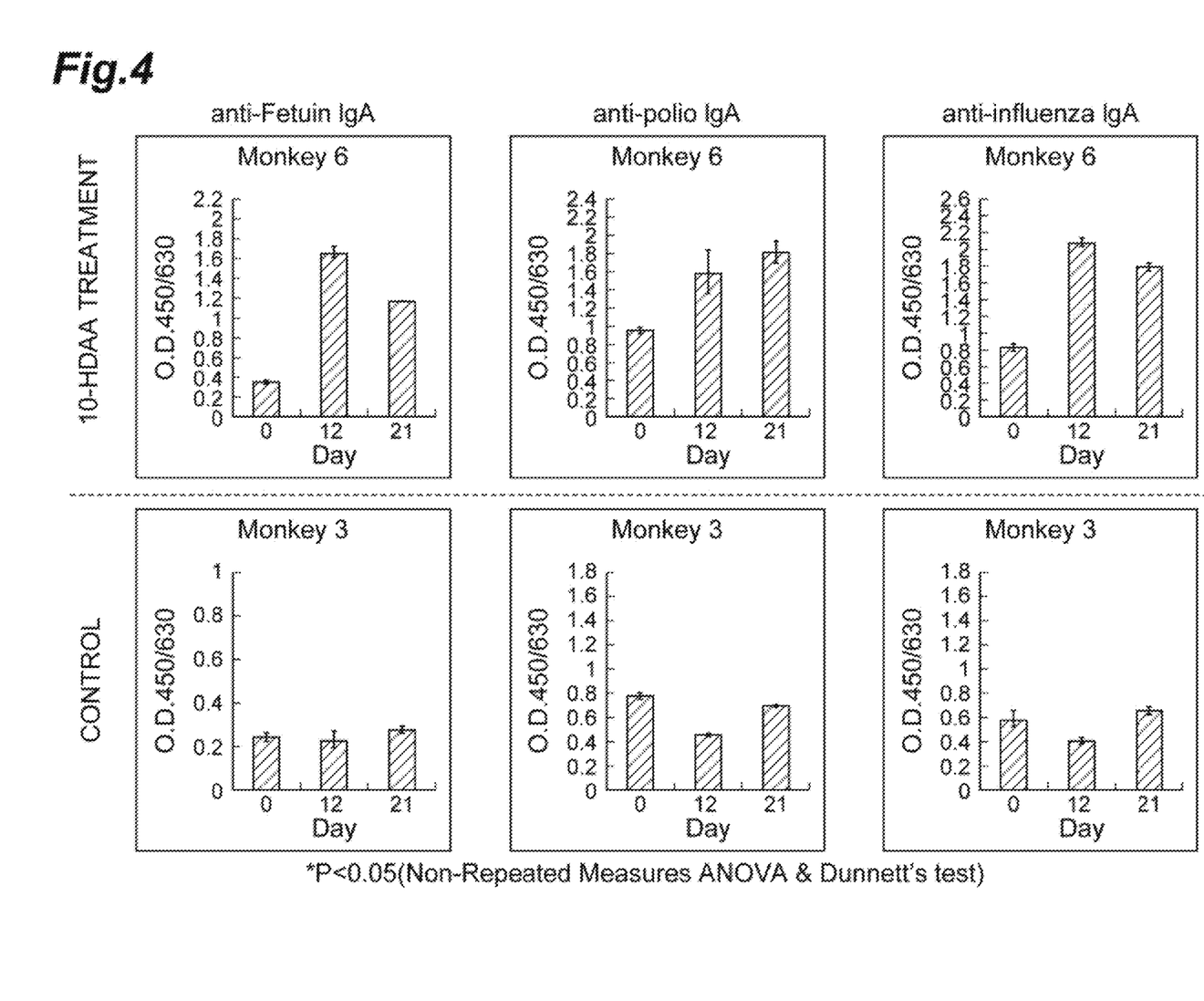
FIG. 4 is graphs showing the measured values of antibody titers.

The anti-Fetuin IgA antibody titer, anti-poliovirus IgA antibody titer, and anti-influenza virus IgA antibody titer in the feces are shown in FIG. 4. As shown in FIG. 4, increases in the anti-Fetuin IgA antibody titer, the anti-poliovirus IgA antibody titer, and the anti-influenza virus IgA antibody titer were observed in the test group, which was sensitized with the antigens about every 3 days while 10-hydroxydecanoic acid was continuously administered once a day. In contrast, such increases in the antibody titers were not observed in the control group, which was sensitized only with the antigens about every 3 days.

These results indicate that GP2 expression induction in in vitro tests correlates with the mucosal immunostimulation effect in vivo.

The invention claimed is:

1. A method for modulating mucosal immunity, the method comprising administering an effective amount of a mucosal immunomodulator to a subject in need thereof, wherein the mucosal immunomodulator comprises, as an active ingredient, at least one selected from the group consisting of compounds represented by the following formulas (5), (6), (7), (8), (9), (10), (11), (12), (13), and (14), and salts thereof, 2. The method according to claim 1, wherein the mucosal immunomodulator comprises as an active ingredient, at least one selected from the group consisting of the compounds represented by the formulas (4), (5), (6), (7) and (8) and salts thereof, and wherein the method is for stimulating the mucosal immunity.

3. The method according to claim 1, wherein the mucosal immunomodulator comprises, as an active ingredient, at least one selected from the group consisting of the compounds represented by the formulas (9), (10), (11), (12), (13), and (14), and salts thereof, and wherein the method is for suppressing the mucosal immunity.

4. The method according to claim 1, wherein the mucosal immunomodulator is administered in the form of a food composition.

5. The method according to claim 2, wherein the mucosal immunomodulator is administered in the form of an adjuvant.

6. The method according to claim 2, wherein the mucosal immunomodulator is administered in the form of a vaccine formulation.

7. An adjuvant comprising a mucosal immunostimulator comprising, as an active ingredient, at least one selected from the group consisting of compounds represented by the following formulas (5), (7), and (8) and salts thereof:

8. A vaccine formulation comprising the adjuvant according to claim 7.

9. An adjuvant comprising a mucosal immunostimulator comprising, as an active ingredient, at least one selected from the group consisting of compounds represented by the following formulas (4) and (6) and salts thereof, and
wherein the adjuvant further comprises a stabilizer and/or a vitamin.

10. A vaccine formulation comprising adjuvant comprising a mucosal immunostimulator, wherein the mucosal immunostimulator comprises, as an active ingredient, at least one selected from the group consisting of compounds represented by the following formulas (4) and (6) and salts thereof, and
wherein the vaccine formulation further comprises an immunogen.

* * * * *